(12) United States Patent
Tachoire et al.

(10) Patent No.: US 7,857,792 B2
(45) Date of Patent: Dec. 28, 2010

(54) CASSETTE FOR IRRIGATION OR ASPIRATION MACHINE FOR ENDOSCOPY

(75) Inventors: Raphael Tachoire, Cagnes-sur-Mer (FR); Stanislas Chautard, Cagnes-sur-Mer (FR); Andre Francisco, Sophia Antipolis (FR); Steven Janin, Nice (FR); Christian Rodriguez, Saint Jeannet (FR); Patrick Janin, Nice (FR); Thierry Pascual, Cagnes-sur-Mer (FR); Armando Dias, Saint Laurent du Var (FR)

(73) Assignee: Future Medical System S.A., Meyrin (CH)

( * ) Notice: Subject to any disclaimer, the term of this patent is extended or adjusted under 35 U.S.C. 154(b) by 877 days.

(21) Appl. No.: 10/591,440

(22) PCT Filed: Mar. 2, 2005

(86) PCT No.: PCT/CH2005/000123
§ 371 (c)(1), (2), (4) Date: Jan. 18, 2007

(87) PCT Pub. No.: WO2005/084728
PCT Pub. Date: Sep. 15, 2005

(65) Prior Publication Data
US 2007/0185433 A1 Aug. 9, 2007

(30) Foreign Application Priority Data
Mar. 5, 2004 (EP) .................................. 04100917
Jun. 18, 2004 (FR) .................................. 04 06620

(51) Int. Cl.
*A61M 5/00* (2006.01)
(52) U.S. Cl. .................................................... 604/246

(58) Field of Classification Search ................... 604/30
See application file for complete search history.

(56) References Cited

U.S. PATENT DOCUMENTS

| 5,246,422 A | 9/1993 | Favre |
| 5,460,490 A | 10/1995 | Carr et al. |

(Continued)

OTHER PUBLICATIONS

International Search Report mailed Aug. 23, 2005 of International Application PCT/CH2005/000123.

*Primary Examiner*—Nicholas D Lucchesi
*Assistant Examiner*—Pritesh Patel
(74) *Attorney, Agent, or Firm*—Westerman, Hattori, Daniels & Adrian, LLP

(57) ABSTRACT

A cassette insertable into an irrigation or aspiration machine for endoscopy includes an irrigation or an aspiration tube and a support provided with one or two inlet plugs and one or two outlet plugs where two tubes form an elbow to be connectable to the inlet or outlet plugs in an input and output direction of motion, respectively and to form an irrigation or aspiration pumping area in the input and output direction of motion. The support includes a T-shaped guide according to the head of the T for protecting the elbow of each tube and according to the length of the T body in a slot guiding the tube in the output direction. The T-shaped guide extends between one or two inlet plugs to form the irrigation or aspiration pumping area on both sides of the slot between each inlet plug and the head of the T.

7 Claims, 18 Drawing Sheets

U.S. PATENT DOCUMENTS

| | | |
|---|---|---|
| 5,626,563 A | 5/1997 | Dodge et al. |
| 5,628,731 A | 5/1997 | Dodge et al. |
| 5,649,905 A | 7/1997 | Zanger et al. |
| 6,817,984 B2 * | 11/2004 | Robinson et al. ........... 604/4.01 |
| 2002/0147423 A1 | 10/2002 | Burbank et al. |
| 2003/0229302 A1 | 12/2003 | Robinson et al. |

* cited by examiner

CASSETTE FOR IRRIGATION OR ASPIRATION MACHINE FOR ENDOSCOPY

TECHNICAL FIELD

The invention pertains to a cassette intended to be inserted into an irrigation or aspiration machine used in endoscopy.

The invention pertains more particularly to a cassette comprising an irrigation tube or an aspiration tube and a support furnished with one or with two inlet plugs, and with one or with two outlet plugs, the tube or the two tubes forming an elbow for engaging with the inlet and outlet plug or the two inlet and outlet plugs in a respectively incoming and outgoing direction of flow and forming a segment of irrigation or of aspiration pumping in the incoming direction of flow.

STATE OF THE ART

A cassette of this type is known from Document U.S. Pat. No. 5,460,490.

According to this document, the pumping segment is provided on the irrigation tube. The aspiration tube does not comprise any pumping segment and must be linked to a suction source to create the aspiration. This arrangement has the drawback of choosing for the pumping segment, the elbow formed by the irrigation tube with respect to the support. Therefore, the elbow remains accessible and is not protected by the support from a risk of wrenching off of the irrigation tube following poor manipulation of the cassette.

A cassette ensuring better protection of irrigation and aspiration tubes is known from Document U.S. Pat. No. 5,628,731. According to this document, the support possesses a base and a cover enclosing the base so as to protect the two tubes. However, it is necessary to open apertures in the base and in the cover in order to liberate the pumping segment formed on the irrigation tube.

Additionally, the irrigation and aspiration tubes are disposed nested the one in the other on one and the same plane of the base of the support. This arrangement tends to impose all the greater bulkiness of the cassette as a second aspiration tube, in general desired by the surgeon using the cassette, must be engaged on the support.

The aim of the invention is to modify a cassette in accordance with that just described above so as to guarantee good protection of irrigation and aspiration tubes while reducing the number of pieces necessary for the support for the engagement of the tubes and while making if possible to engage a bypass aspiration tube without increasing the general bulkiness of the cassette.

DISCLOSURE OF THE INVENTION

Accordingly, the subject of the invention is a cassette intended to be inserted into an irrigation or aspiration machine used in endoscopy comprising an irrigation tube or an aspiration tube and a support furnished with one or with two inlet plugs and with one or with two outlet plugs, the tube or the two tubes forming an elbow for engaging with the inlet and outlet plug or the two inlet and outlet plugs in a respectively incoming and outgoing direction of flow and forming a segment of irrigation or of aspiration pumping in the incoming direction of flow, characterized in that the support comprises a T guide shaped to the head of the T so as to protect the elbow of each tube and shaped along the body of the T as a slot guiding the tube or the two tubes in the outgoing direction of flow, the T guide running between the inlet plug or the two inlet plugs so as to form the segment of irrigation or of aspiration pumping on either side of the slot between each inlet plug and the head of the T.

The T guide makes it possible to protect the tube or the two tubes in the two directions of flow incoming and outgoing without it being necessary to provide the support with a cover. The slot guides the tube or the two tubes, while allowing them to be placed one above the other so as to reduce the bulkiness of the cassette by comparison with a disposition of two tubes in one and the same plane. By extending between the two inlet plugs of the tubes, the T guide makes it possible additionally to form a pumping segment for each of the two irrigation and aspiration tubes.

BRIEF DESCRIPTION OF THE DRAWINGS

Other advantages of the invention will become apparent on reading the description of an embodiment illustrated hereinbelow by the drawings.

FIG. 2 shows the cassette end-on.

TABLE 1

Figure 1:
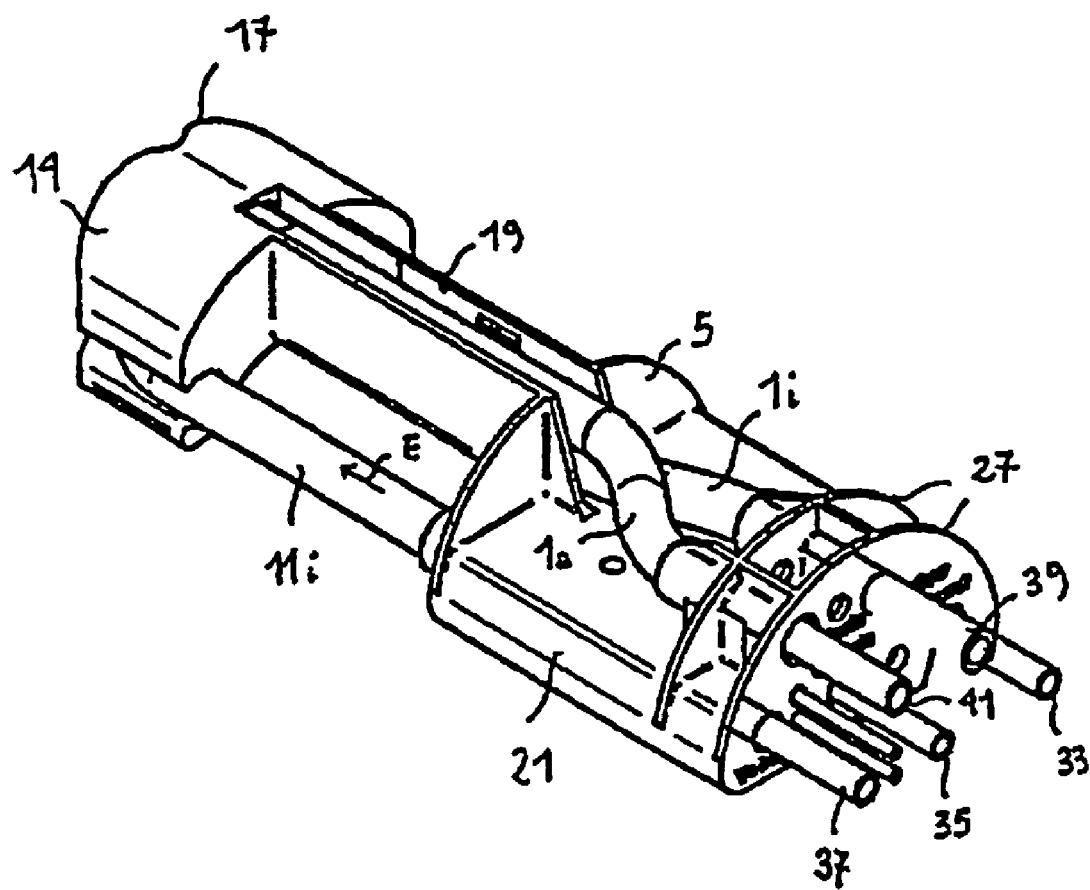
FIG. 1 shows in perspective a cassette according to the invention.
Figure 2:
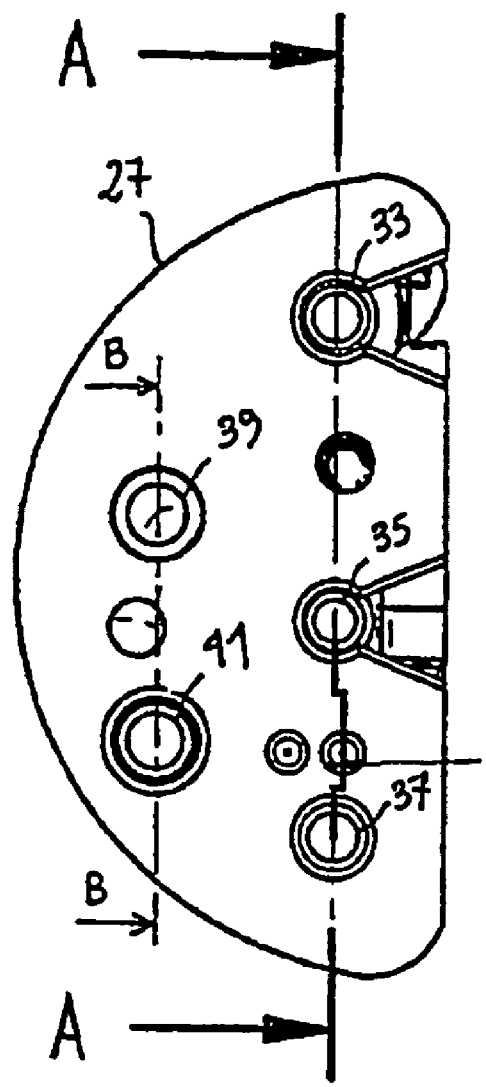
Figure 3:
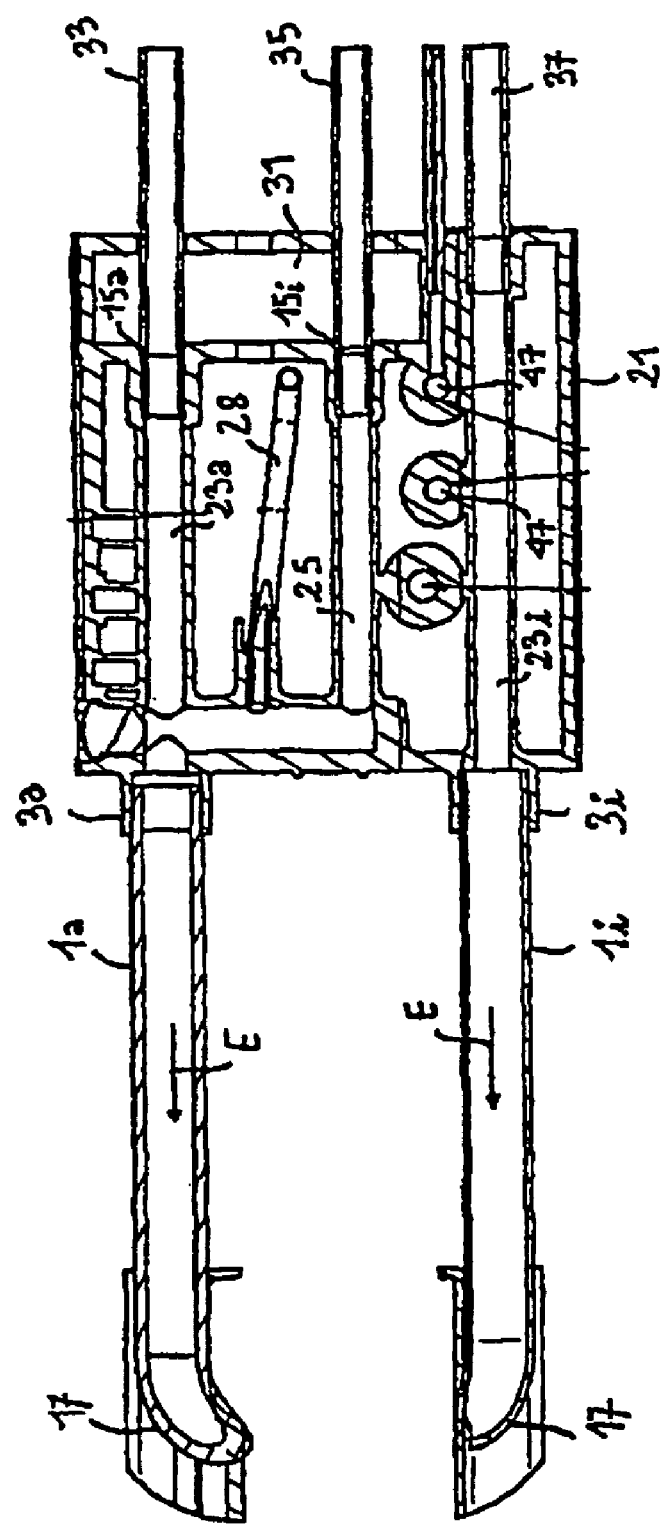
FIG. 3 shows the cassette in a cross section A-A.
Figure 4:
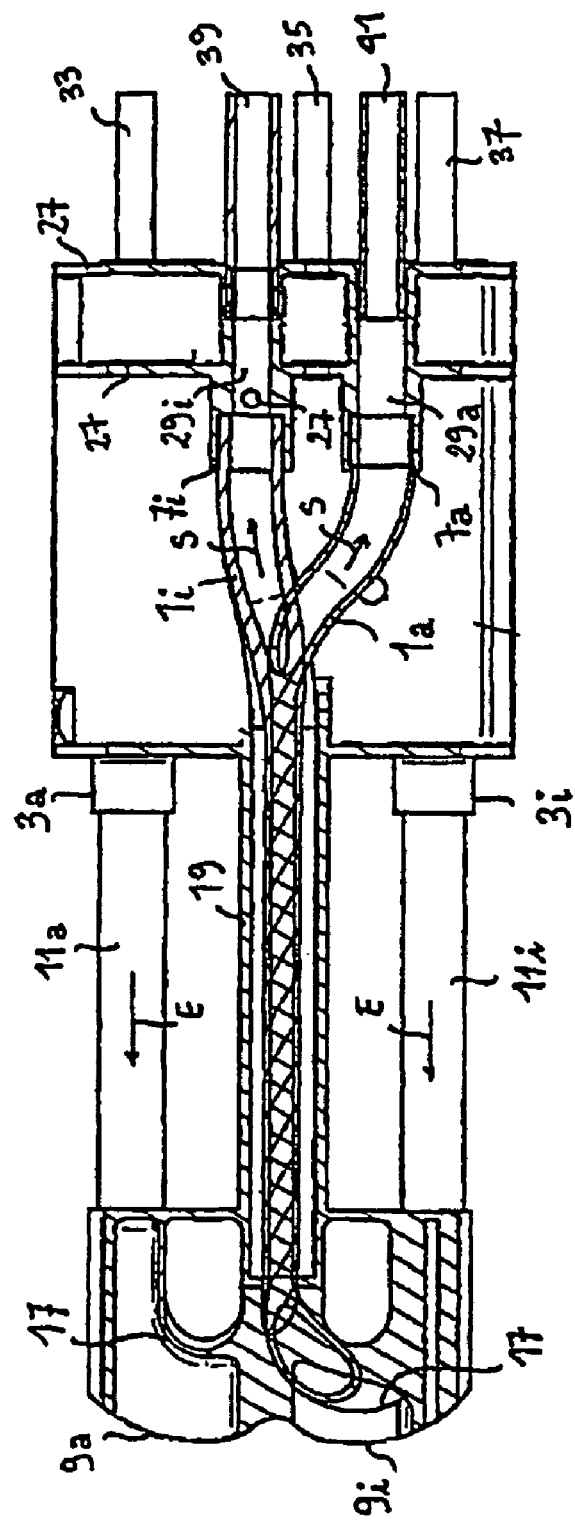
FIG. 4 shows the cassette in a cross section B-B.
Figure 5:
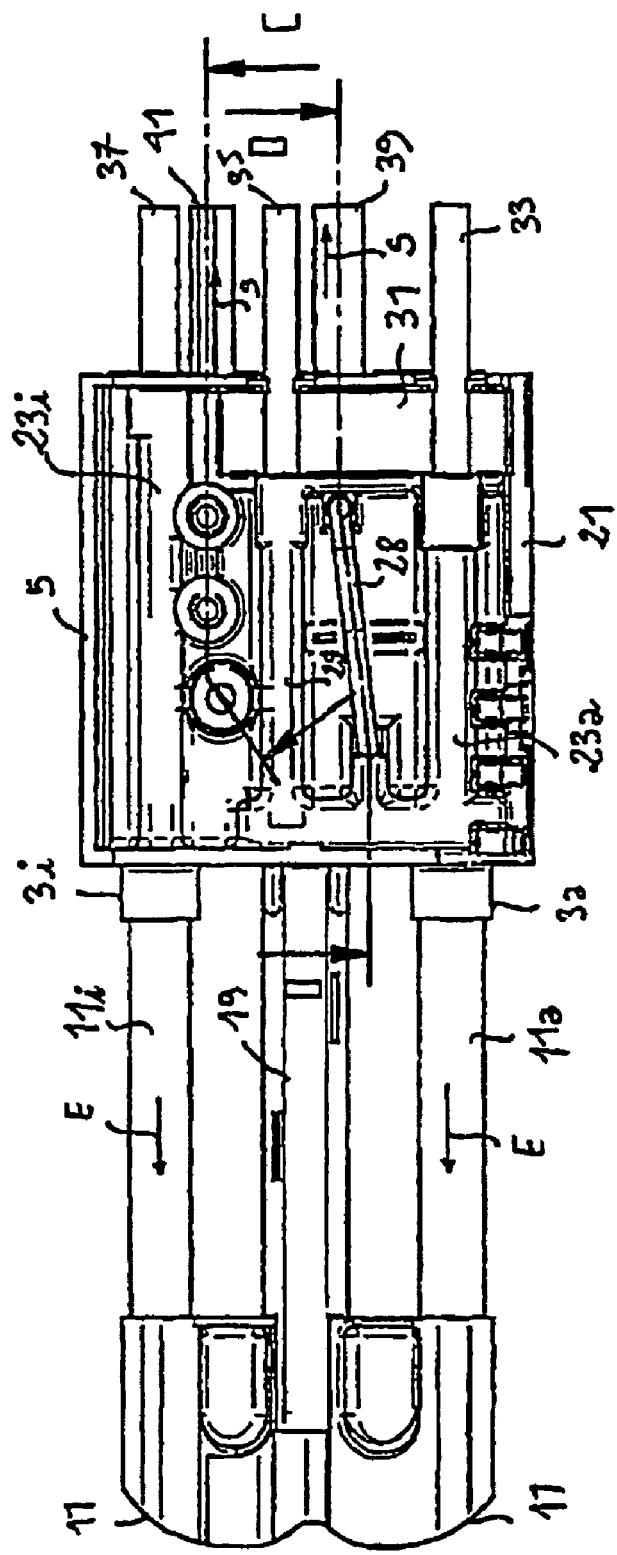
FIG. 5 shows the cassette in a view from below.
Figure 6:
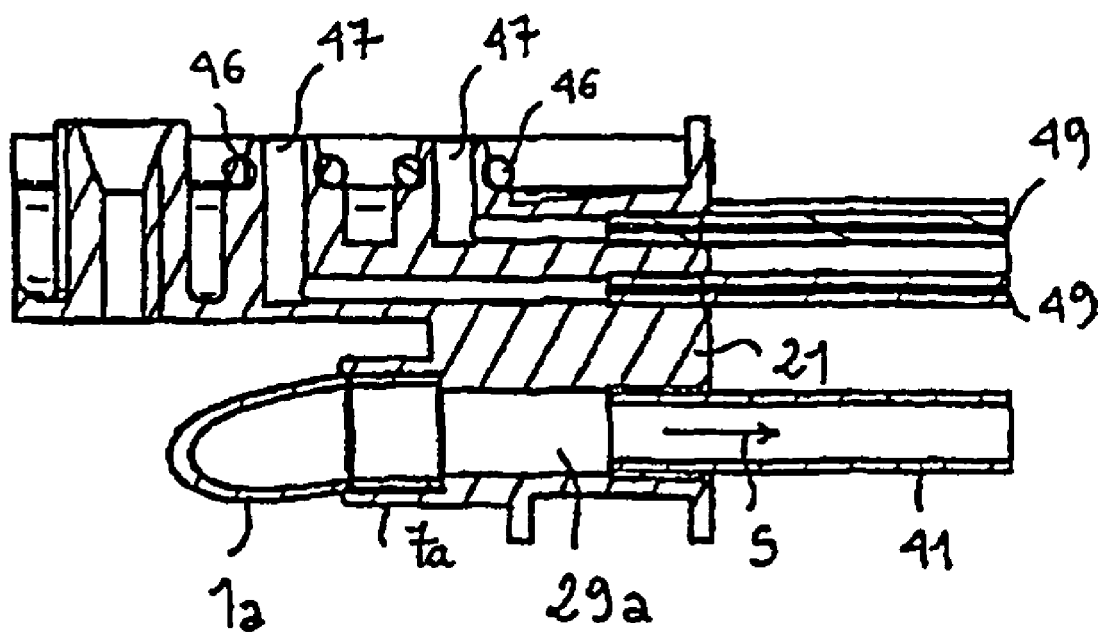
FIG. 6 shows the cassette in a cross section C-C.
Figure 7:
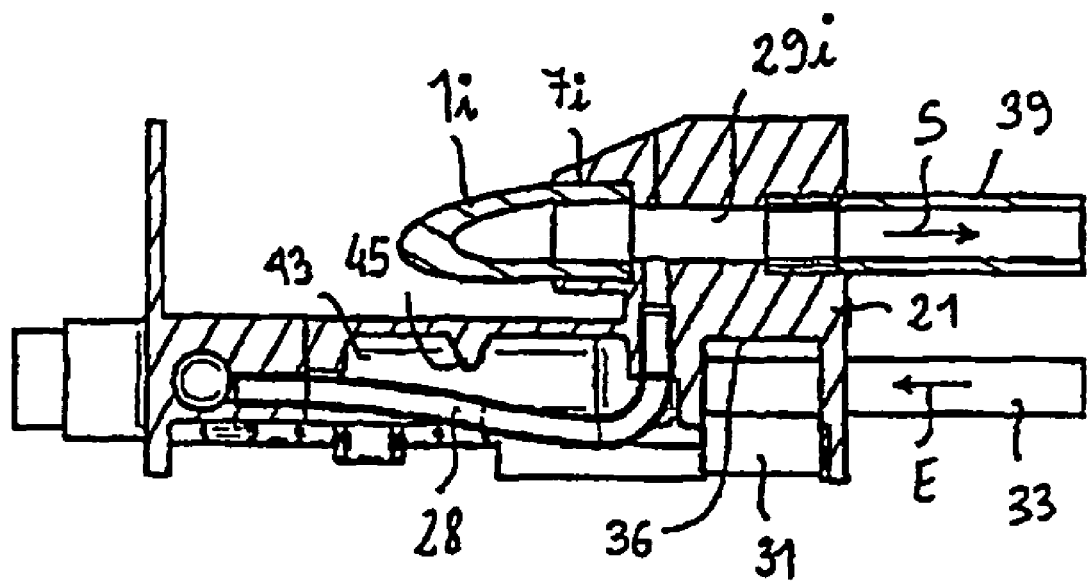
FIG. 7 shows the cassette in a cross section D-D.

| | |
|---|---|
| 1i, 1a | Irrigation, aspiration tube |
| 3i, 3a | Inlet plugs |
| 5 | Support |
| 7i, 7a | Outlet plugs |
| 9i, 9a | Elbows |
| 10i, 10a | Irrigation, aspiration tube pieces |
| 11i, 11a | Irrigation, aspiration pumping segment |
| 13 | T guide |
| 14 | Protective hood |
| 15i, 15a | Inlet ends |
| 17 | Rounding |
| 19 | Slot |
| 21 | Housing |
| 23i, 23a | Inlet channels |
| 25 | Third inlet channel |
| 26 | End |
| 27 | Supports in the form of half-disks |
| 28 | Communication pathway |
| 29i, 29a | Outlet channels |
| 31 | Chamber |
| 33, 35 | Complementary aspiration tubes |
| 36 | Back wall |
| 37, 39 | Complementary irrigation tubes |
| 41 | Complementary aspiration tube |

TABLE 1-continued

| | |
|---|---|
| 43 | Chamber |
| 45 | Back wall |
| 47 | Pressure plugs |
| 48 | Elastomer piece |
| 49 | Pressure lines |
| 51i, 51a | Peristaltic irrigation, aspiration pump |
| 53i, 53a | Shoes |
| 54i, 54a | Wheels |
| 55i, 55a | Rollers |
| 61 | Chassis |
| 62 | Compression springs |
| 63 | Carriage |
| 64 | Abutment |
| 65 | Cassette holder |
| 66 | Position sensor |
| 67a, 69a | Shutters |
| 68 | Position sensors |
| 71 | Third shutter |
| 73 | Means of locking |
| 75 | Abutment |
| 77 | Recognition fingers |
| 79 | Centering means |
| 83 | Runners |
| 85 | Linear actuator |
| 86 | Rod |
| 87 | Runners |
| 88 | Position sensors |
| 89 | Runners |
| 90 | Position sensors |
| 91 | Springs |
| 93 | Runners |
| 94 | Linear actuators |
| 95 | Teats |
| 96 | Linear actuator |

EMBODIMENT(S) OF THE INVENTION

With reference to FIGS. 1 to 7, a cassette intended to be inserted into an irrigation and aspiration machine used in endoscopy comprises an irrigation tube 1i, an aspiration tube 1a and a support 5 furnished with two inlet plugs 3i, 3a and two outlet plugs 7i, 7a. The two tubes together form an elbow 9i, 9a for engaging with the two inlet and outlet plugs in a respectively incoming E and outgoing S direction of flow and form one or the other a segment of irrigation 11i or aspiration 11a pumping in the incoming direction E of flow.

According to the invention, the support 5 comprises a T guide 13 shaped to the head of the T so as to protect the elbow 9i, 9a of each tube 1i, 1a and shaped along the body of the T as a slot 19 guiding the two tubes superposed one 1i with respect to the other 1a in the outgoing direction of flow S.

In the example illustrated by FIGS. 1 to 7, the head of the T comprises a protective hood 14 and forms a double rounding 17 for guiding the two elbows 9i, 9a of each tube.

Figure 8:
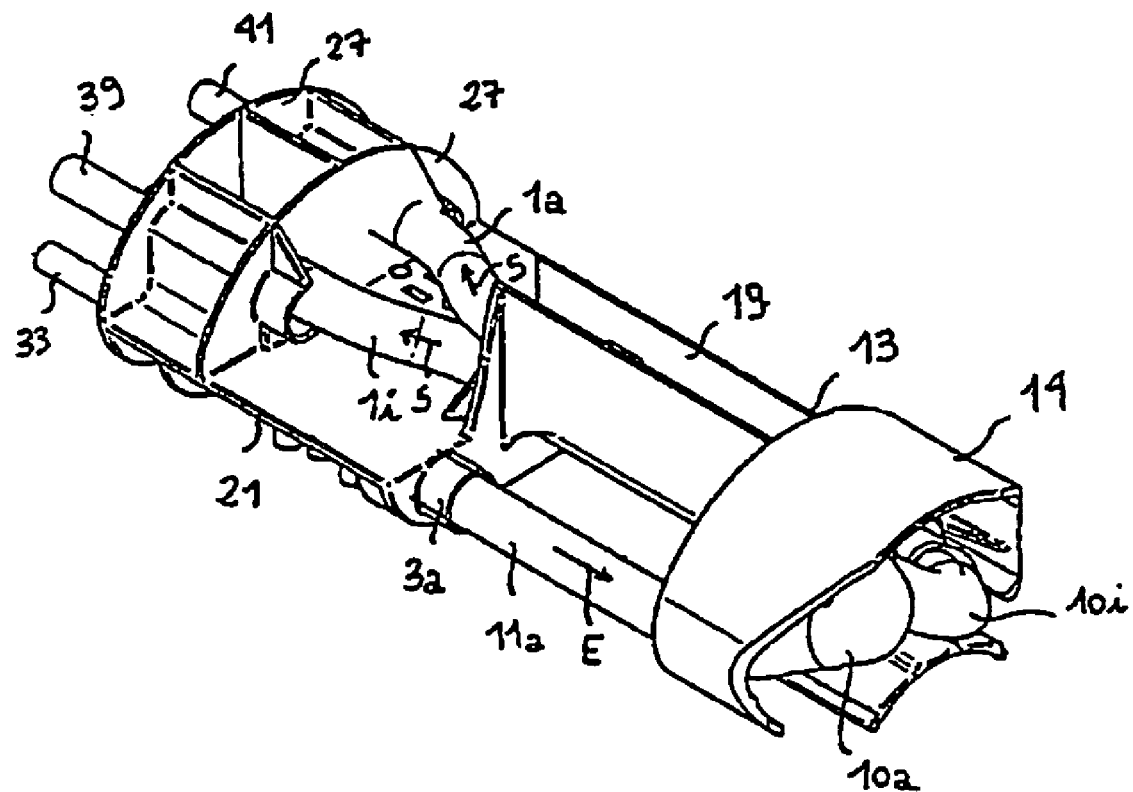
FIG. 8 shows another exemplary embodiment of a cassette according to the invention.

In the example of FIG. 8, the head of the T here again comprises a protective hood 14 but the elbows 9i, 9a are formed by tubular pieces 10i, 10a manufactured from a flexible plastic and inserted between two portions of each irrigation and aspiration tube.

The T guide 13 extends between the two inlet plugs 3i, 3a to form the segment of irrigation 11i or aspiration 11a pumping on either side of the slot 19 between each inlet plug 3i, 3a and the head of the T.

The T guide 13 is fixed to a housing 21 integrated with the support 5 and provided with two inlet channels 23i, 23a open at an inlet end 15i, 15a and emerging at an opposite end via the inlet plug 3i or the inlet plugs 3i, 3a so as to ensure communication with the tube 1i or the two tubes 1i, 1a in the incoming direction of flow E.

The housing 21 is provided with a third inlet channel 25 open at one end 26 and disposed bypass-wise with respect to the inlet channel 23a communicating with the aspiration tube 1a so as to emerge, at an opposite end, via the inlet plug 3a ensuring communication with the aspiration tube 1a.

The inlet channel 23a communicating with the aspiration tube 1a and the third inlet channel 25 mounted bypass-wise open out, at the opposite end to the inlet plug 3a ensuring communication with the aspiration tube 1a, into a chamber 31 integrated with the housing and receiving two complementary aspiration tubes 33, 35 engaging with these two channels 23a, 25 while being disposed some distance from a back wall 36 of the chamber 31 so as to be compressed against this back wall 36 in a position of obstruction of this inlet channel 23a communicating with the aspiration tube 1a or of this third inlet channel 25.

The housing 21 is provided with two outlet channels 29i, 29a open at an outlet end and emerging at an opposite end via the outlet plugs 7i, 7a so as to ensure communication with the two tubes 1i, 1a in the outgoing direction of flow S.

The outlet channels 29i, 29a are carried by supports 27 in the form of half-disks extending in a plane perpendicular to a plane of the housing so as to be raised up with respect to the inlet channels 23i, 23i, 25.

The housing 21 is provided with a communication pathway 28 between the outlet channel 29i communicating with the irrigation tube 1i and the inlet channel 23a communicating with the aspiration tube 1a or the third inlet channel 25 mounted bypass-wise with respect to the latter.

The communication pathway 28 is ensured by a tube disposed in a chamber 43 integrated with the housing 21 and some distance from a back wall 45 of this chamber so as to be compressed against this back wall in a position of obstruction of this communication pathway.

In the example illustrated by FIGS. 1 to 7, the housing 21 incorporates one or two pressure plugs 47 formed from conduits for the passage of air originating from pressure lines 49 connected up to a complementary irrigation tube 39 by way of a pressure detector with membrane.

Figure 9:
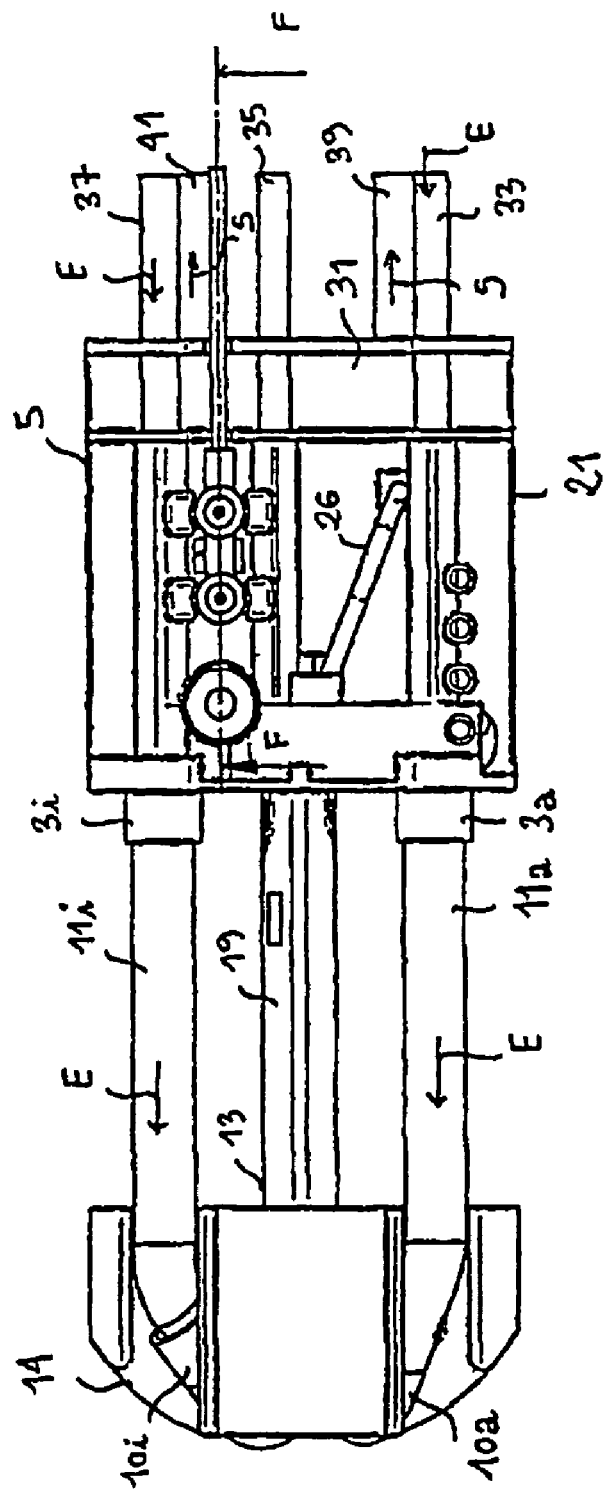
FIG. 9 shows the cassette of FIG. 8 in a view from below.

In the example illustrated by FIG. 9, the housing 21 is designed to receive an elastomer piece 48 forming in one piece, the two pressure plugs 47 and the conduits for the passage of air originating from the pressure lines 49.

Figure 10:
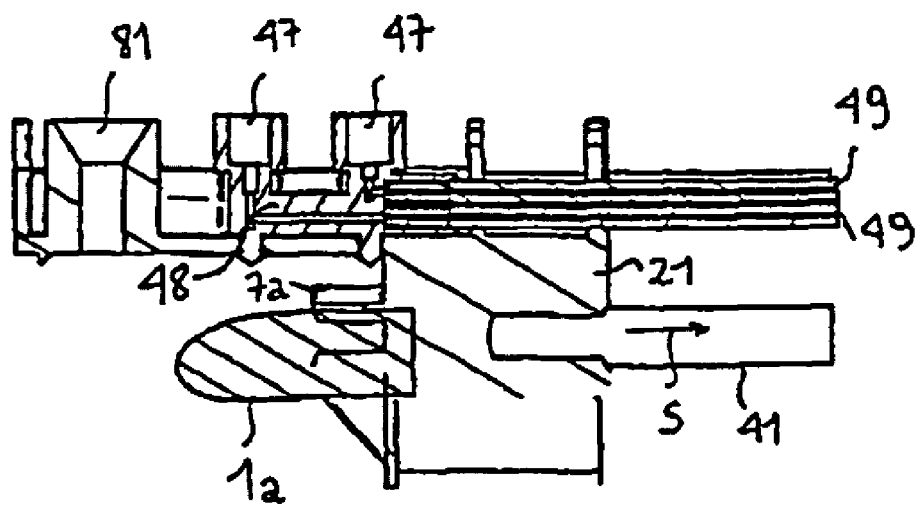
FIG. 10 shows the cassette of FIG. 8 in a section F-F.
Figure 11:
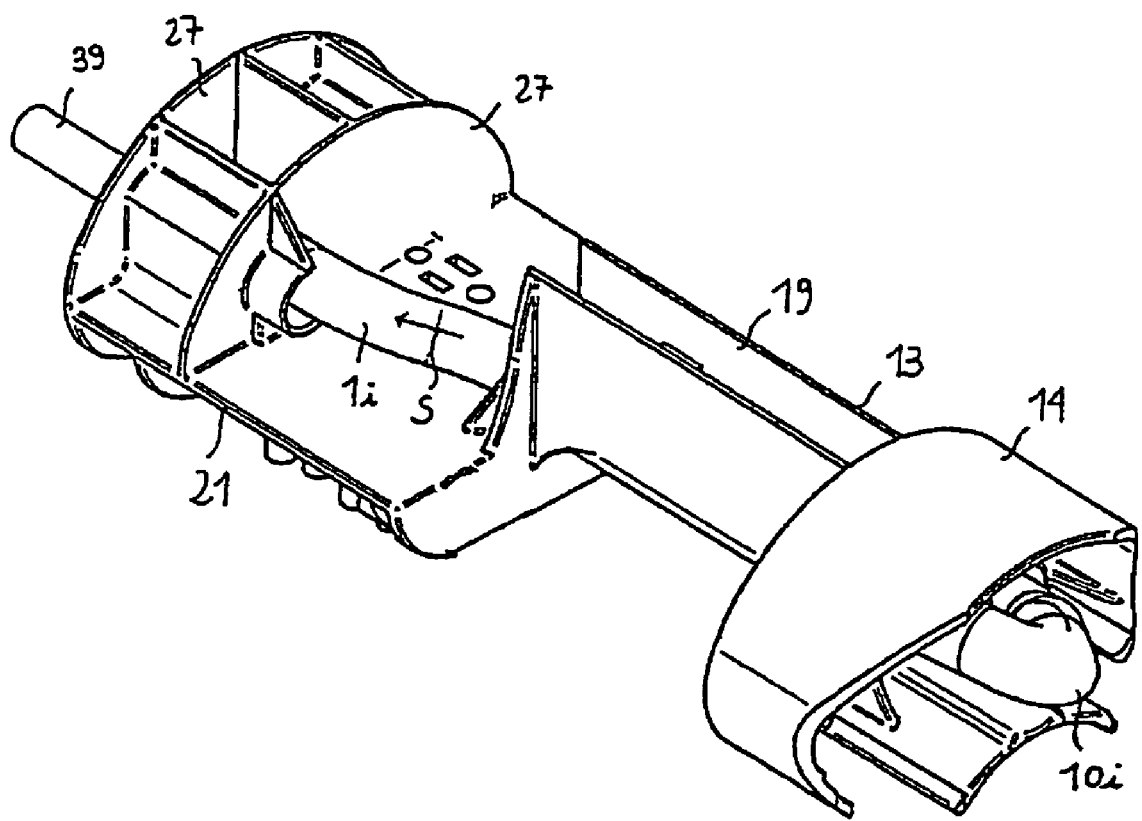
FIG. 11 shows an exemplary embodiment of a cassette according to FIG. 8, in which the aspiration function has been removed, leaving only the irrigation function.
Figure 12:
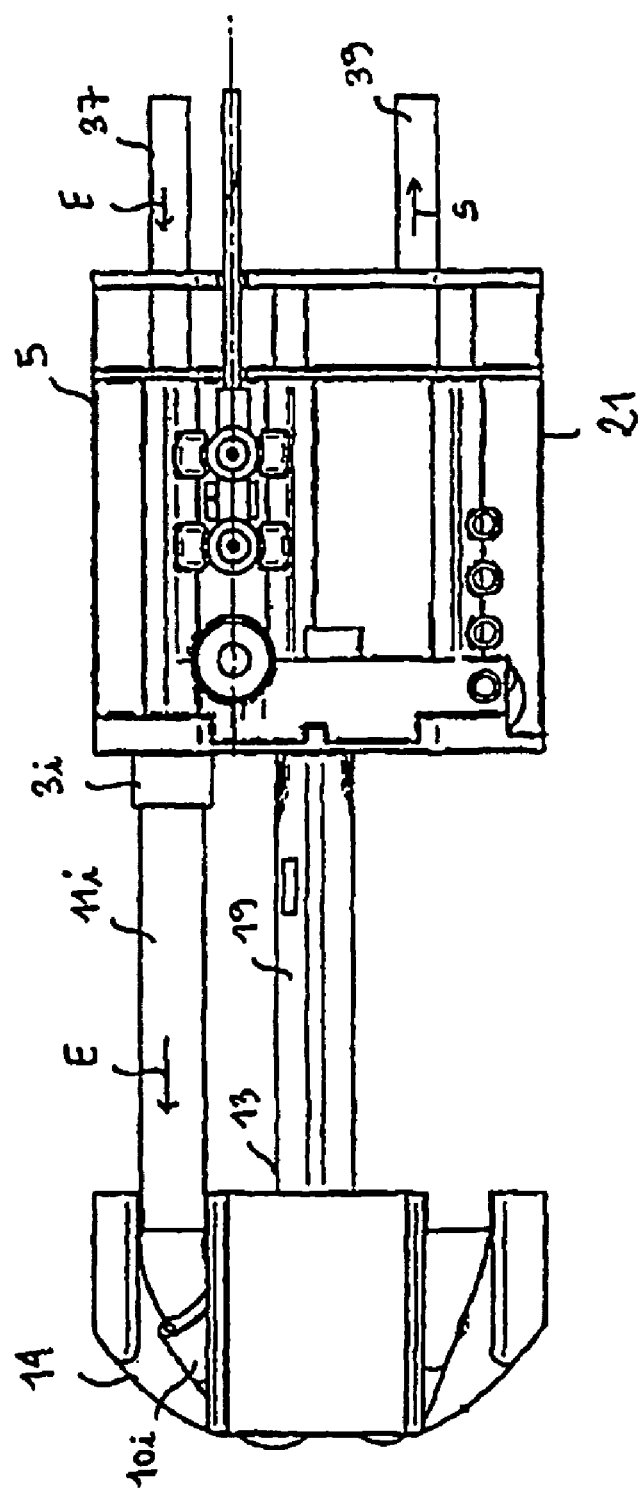
FIG. 12 shows the cassette of FIG. 11 in a view from below.
Figure 13:
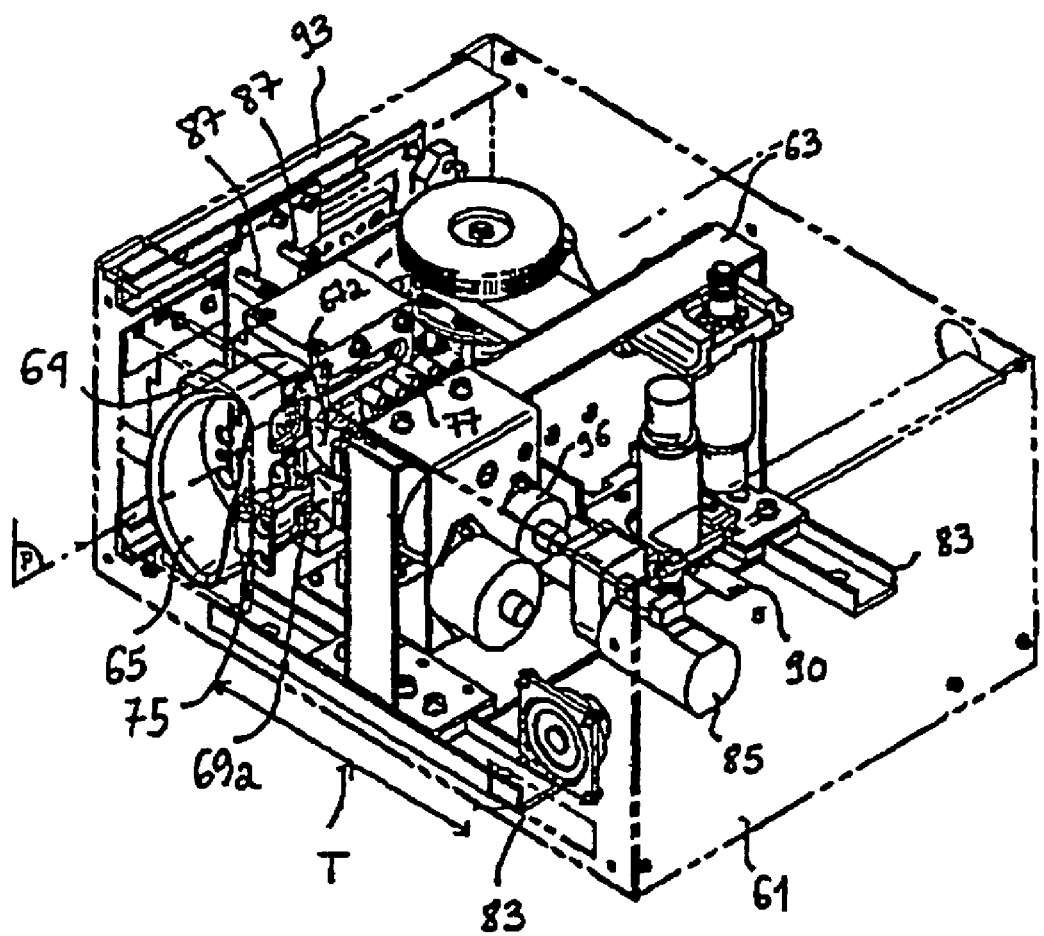
FIG. 13 shows in perspective an irrigation and aspiration machine according to the invention in which a cassette according to the invention is inserted.
Figure 14:
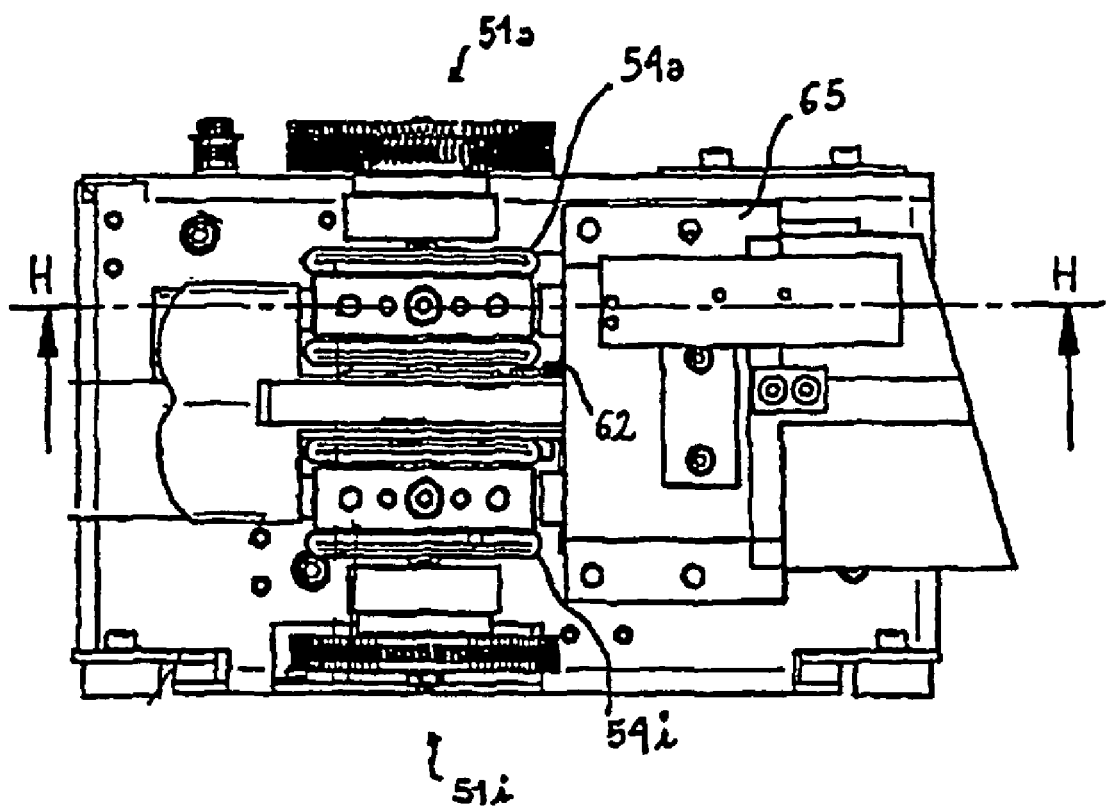
FIG. 14 shows in a view from above a carriage and a cassette holder of the machine illustrated by FIG. 13.
Figure 15:
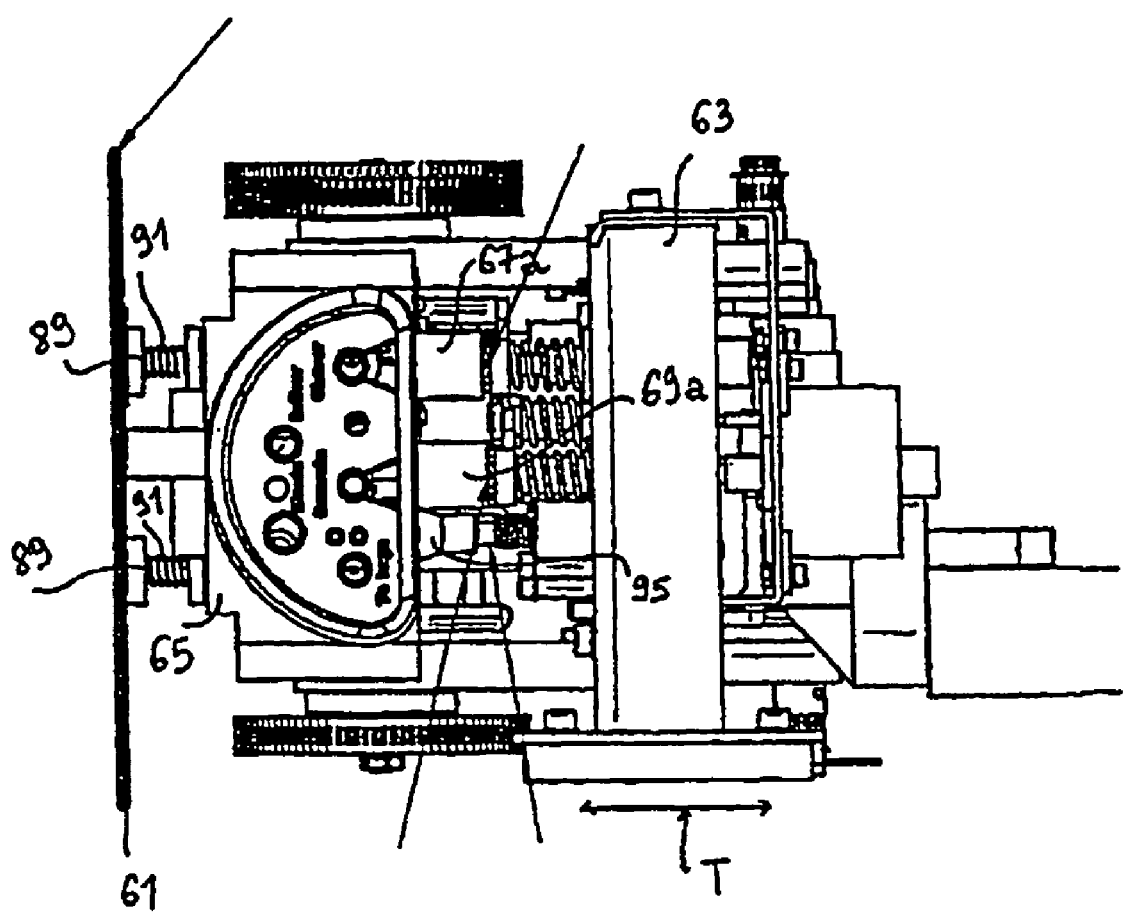
FIG. 15 is a side view of FIG. 14.
Figure 16:
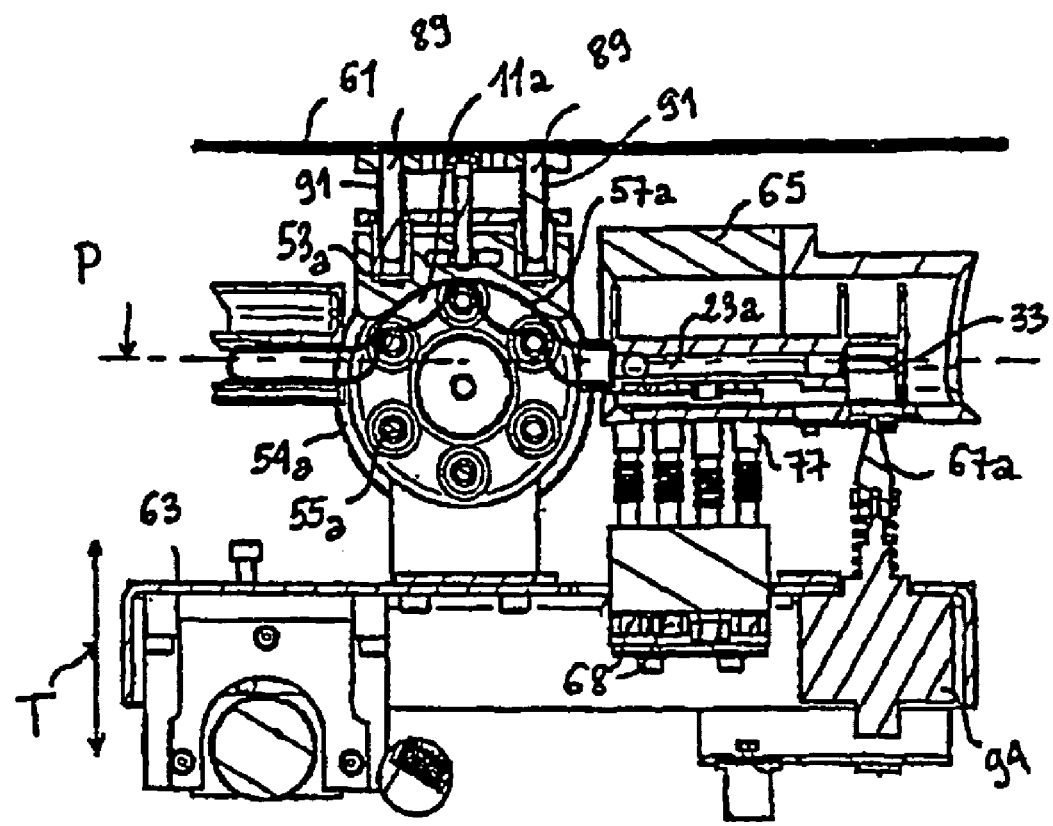
FIG. 16 is a view on the section H-H of FIG. 14.
Figure 17:
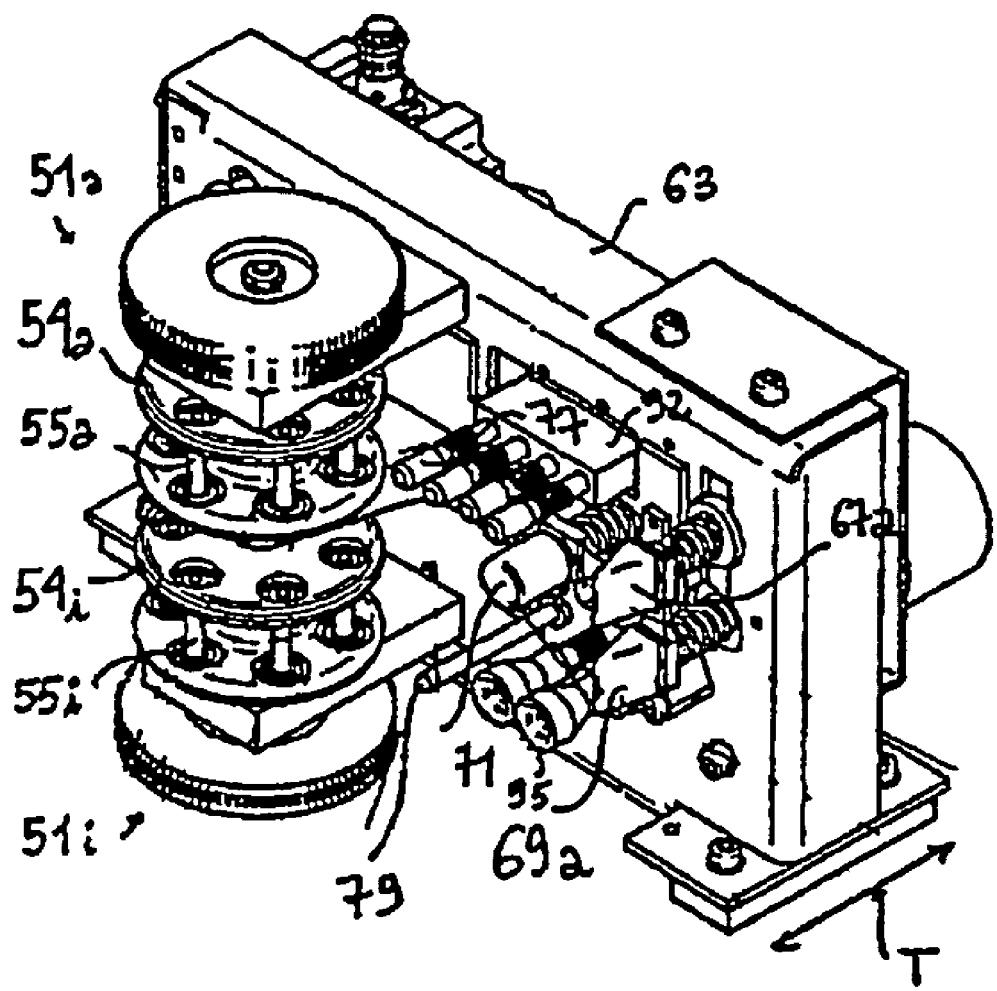
FIG. 17 shows more particularly the carriage of FIG. 13.
Figure 18:
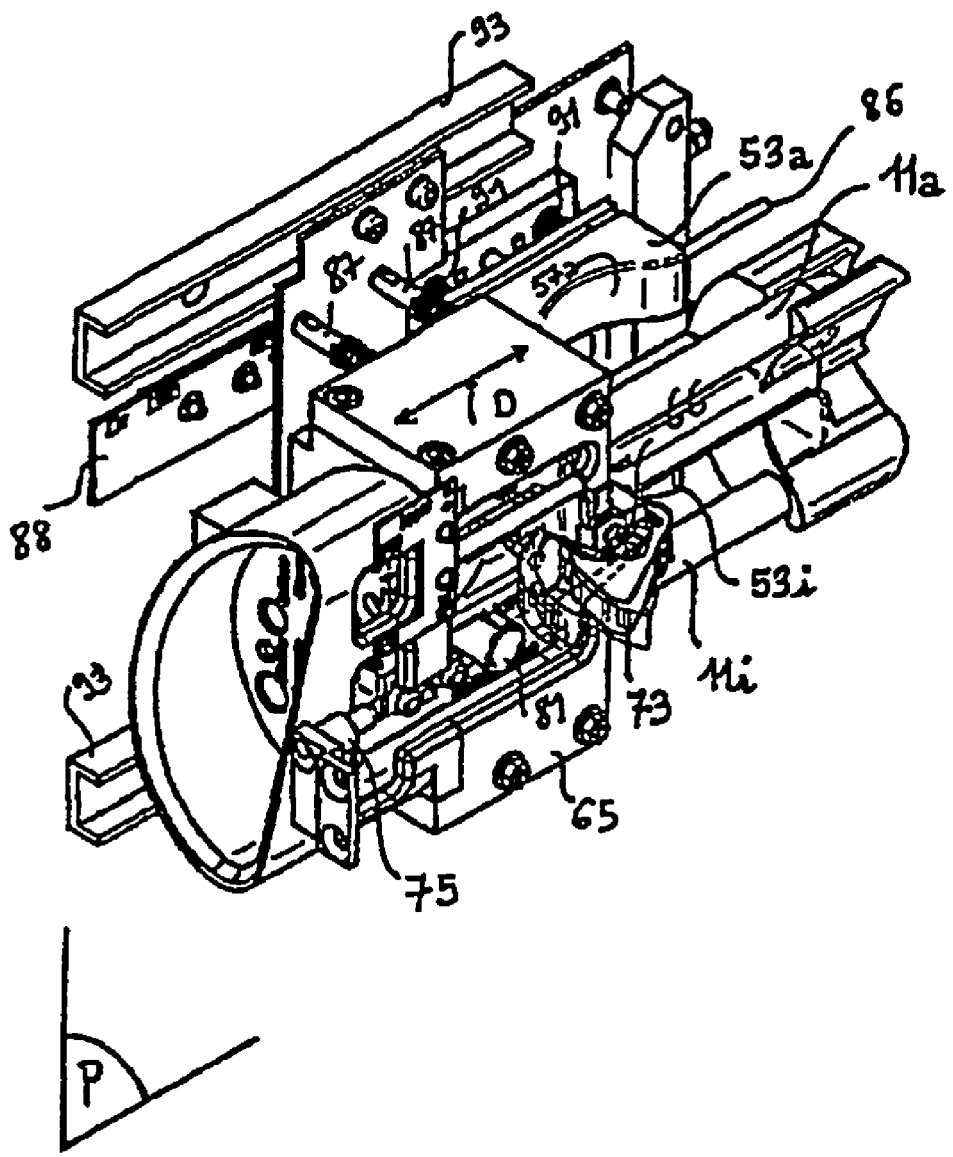
FIG. 18 shows more particularly the cassette holder of FIG. 13.

In the example illustrated by FIGS. 11 and 12, the aspiration tube 1a, the inlet plug 3a and the aspiration pumping segment 11a have been removed with respect to the exemplary embodiment illustrated by FIGS. 8 to 10. In the housing 21, the aspiration channel 23a, the outlet channel 29a and also the complementary aspiration tubes 33, 35 and 41 have likewise been removed. In this exemplary embodiment, the cassette according to the invention allows only irrigation to be carried out and is more particularly suitable for use in endoscopy for diagnostic purposes.

The invention extends to an irrigation and aspiration machine with cassette used in endoscopy.

With reference to FIGS. 13 to 18, the machine comprises a peristaltic irrigation pump 51i with shoe 53i and with wheel 54i with rollers 55i mounted in correspondence, one 53i on a chassis 61 and the other 54i on a carriage 63 moveable along runners 83 fixed to the chassis 61 so as to extend in a direction of translation T. A linear actuator 85 controls the translation of the carriage 63 between a rest position by unclamping of the shoe 53i with respect to the runners 55i and a pumping position by reclamping of the shoe 53i with respect to the rollers 55i. The machine also comprises a cassette holder 65 mounted on the chassis 61 so as to extend in a plane P perpendicular to the direction of translation T and passing between the shoe 53i and the wheel 54i with rollers 55i of the irrigation pump 51i.

According to the invention, the machine comprises a peristaltic aspiration pump 51a with shoe 53a and with wheels 54a with rollers 55a mounted in correspondence, one 53a on the chassis 61 and the other 54a on the carriage 63 so as to unclamp or reclamp said shoe 53a with respect to said rollers 55a in the direction of translation T upon the unclamping or reclamping of the shoe 53i with respect to the rollers 55i of the peristaltic irrigation pump 51i between the rest position and the pumping position, the plane P perpendicular to the direction of translation T passing likewise between the shoe 53a and the wheel 54a with rollers 55a of the aspiration pump.

The arrangement of the cassette holder 65 in a plane perpendicular to the direction of translation T of the moveable carriage 63 makes it possible to dispose at one and the same time the irrigation pumping segment 11i and the aspiration pumping segment 11a of a cassette according to the invention between the shoes 53i, 53a and the rollers 55i, 55a respectively of the peristaltic irrigation pump 51i and the peristaltic aspiration pump 51a. The cassette according to the invention is introduced into the cassette holder 65 when the shoes are unclamped with respect to the rollers in the rest position so that the irrigation 11i and aspiration 11a pumping segments are thereafter laminated between the shoes and the rollers in the pumping position.

Preferably, the cassette holder 65 is mounted moveably with respect to the chassis 61 so as to be driven in displacement by the carriage 63 when the latter is displaced from the rest position to the pumping position. The displacement of the cassette holder 65 takes place along runners 87 fixed to the chassis 61 parallel to the direction of translation T.

Advantageously, the shoes 53i, 53a of the peristaltic irrigation 51i and aspiration 51a pumps are mounted moveably with respect to the chassis 65 along runners 89 extending parallel to the direction of translation T. The displacement of the shoes 53i, 53a takes place against the compression of springs 91 disposed about the runners 89 so as to adjust a laminating pressure between the shoes 53i, 53a and the rollers 55i, 55a when the carriage 63 has displaced into the pumping position.

To facilitate the introduction or the removal of a cassette according to the invention into or from the irrigation and aspiration machine, the cassette holder 65 is mounted moveable along runners 93 fixed to the chassis 61 so as to be displaced parallel to the plane P perpendicular to the direction of translation T. The displacement of the cassette holder 65 is controlled by a linear actuator between a cassette insertion position in which the cassette holder 65 is near to the shoes and wheels with rollers of the irrigation and aspiration pumps and a cassette ejection position in which the cassette holder 65 is away from said shoes and said wheels with rollers.

The irrigation and aspiration machine with cassette furthermore comprises a means of centering 79 mounted on the carriage 63 so as to be displaced with the carriage 63 in the direction of translation T from the rest position to the pumping position and after the cassette holder has come near to the shoes 53i, 53a and the wheels 54i, 54a with rollers of the two irrigation and aspiration pumps in the cassette insertion position.

INDUSTRIAL APPLICATION

The support 5 of a cassette according to the invention as well as the T guide 13 with the protective hood 14 and the head of the T and the slot 21 along the body of the T, the housing integrated with the support 21 provided with the inlet channels 23i, 23a, the third inlet channel 25, the inlet plugs 3i, 3a, the outlet plugs 7i, 7a and the supports 27 are in one piece preferably of injection molded plastic.

The use of the cassette and of the irrigation and aspiration machine according to the invention takes place in the following manner. The cassette is introduced by hand into the cassette holder 65 until a means of locking 73 mounted pivotably with respect to the cassette holder 65 locks the support 5 of the cassette with respect to the cassette holder 65 against the compression of springs 62 carried by the cassette holder. The pivoting of the means of locking 73 is detected by a position sensor 66 fixed to the cassette holder 65.

It should be noted that the protective hood 14 and the supports in the form of half-disks 27 offer a function for advising a user upon the insertion of the cassette into the cassette holder 65.

The linear actuator controlling the displacement of the cassette holder 65 displaces the latter into the cassette insertion position so as to dispose the irrigation 11i and aspiration 11a pumping segments of the irrigation 1i and aspiration 1a tubes between the shoes 53i, 53a and the wheels 54i, 54a with rollers respectively of the irrigation pump and of the aspiration pump. Position sensors 88 are fixed to the chassis 61 so as to monitor the displacement of the cassette holder 65 in the plane P perpendicular to the direction of translation T. A rod 86 is fixed to the linear actuator controlling the displacement of the cassette holder 65 so as to come into abutment against the chassis and stop the displacement of the cassette holder in the position of insertion of the cassette.

The linear actuator 85 controlling the displacement of the moveable carriage 63 thereafter displaces the latter in the direction of translation T from the rest position to the pumping position so as to displace the cassette holder 65 and press the irrigation 1i and aspiration 1a pumping segments of the cassette between the shoes and the rollers respectively of the irrigation pump and of the aspiration pump. Position sensors 90 are fixed to the chassis 61 to monitor the displacement of the carriage 63 in the direction of translation T. The shoes 53i, 53a of the peristaltic irrigation and aspiration pumps displace against the compression of the springs 91 disposed about the runners 87 so as to adjust a laminating pressure between the shoes 53i, 53a and the rollers 55i, 55a when the carriage 63 has displaced into the pumping position. The centering means 79 carried by the moveable carriage 63 insert themselves into a centering means 81 carried by the housing 21 of the cassette so as to center the cassette with respect to the carriage 63 in the pumping position.

Advantageously, the carriage 63 carries cassette recognition fingers 77 moveable with respect to the carriage in the direction of translation T. The cassette recognition fingers 77 are displaced by the carriage parallel to the direction of translation T so as to cooperate with corresponding tags formed in the housing 21 of the cassette so as to recognize the latter in the pumping position and thus preadjust certain operating parameters of the irrigation and aspiration machine, in particular the speed of rotation of the wheel with rollers of the irrigation pump. Position sensors 68 are provided on the chassis 63 for detecting the presence or the absence of the cassette recognition fingers 77 and thus identify the cassette inserted into the irrigation and aspiration machine.

The irrigation tube 1i is supplied with physiological fluid from a reservoir and a complementary irrigation tube 37 engaging in the inlet channel 3i of the housing 21. The pumping segment 11i of the irrigation tube 1i cooperates with the peristaltic irrigation pump 51i disposed in the irrigation and aspiration machine in which the cassette is inserted to set the physiological fluid into flow in the complementary irrigation tube 39 engaging in the outlet channel 29$i$ communicating with the irrigation tube 1$i$ and emerging into an endoscope cannula placed in a zone of surgical intervention of a patient, for example a joint of the knee or of the shoulder.

The pumping segment 11$a$ of the aspiration tube 1$a$ cooperates with the peristaltic aspiration pump 51$a$ disposed in the irrigation and aspiration machine so as to aspirate, into the aspiration tube 1$a$, a fluid originating either from a cannula or from another surgical tool, for example a "shaver", by way respectively of the complementary aspiration tubes 33 and 35, one being compressed so as to be obstructed when the other is in service. For this purpose, the carriage 63 carries two shutters 67$a$, 69$a$ moveable with respect to the carriage 63 in the direction of translation T. Linear actuators 94 control the displacement of one or the other of the shutters so as to compress one or the other of the complementary aspiration tubes 33, 35 against the back wall 37 of the chamber 31 integrated with the housing 21 of the cassette in the position of obstruction of the inlet channel 23$a$ communicating with the aspiration tube 1$a$ or in the position of obstruction of the third inlet channel 25 mounted bypass-wise with respect to this inlet channel 23$a$.

The aspirated fluid flows towards a receptacle outside the irrigation and aspiration machine by way of a complementary aspiration tube 41 engaging in the outlet channel 29$a$ communicating with the aspiration tube 1$a$.

The communication pathway 28 between the outlet channel 29$i$ communicating with the irrigation tube 1$i$ and the inlet channel 23$a$ communicating with the aspiration tube 1$a$ or the third inlet channel 25 mounted bypass-wise with respect to the latter is controlled from a position of obstruction to a position of flow so as to manage an accidental overpressure in the patient's joint. For this purpose, the moveable carriage 63 carries a third shutter 71 moveable with respect to the carriage 63 in the direction of translation T. A linear actuator 96 controls the displacement of the third shutter so as to compress the communication tube 28 against the back wall 45 of the chamber 43 integrated with the housing 21 in the position of obstruction of this communication tube 28.

Advantageously, the moveable carriage 63 carries one or two air pressure plugs formed of teats 95 communicating with pressure sensors fixed for example to the chassis 61 so as to determine the pressure detected for example on the complementary irrigation tube 39 by a detector with membrane. The teats 95 are disposed on the moveable carriage 63 so as to be inserted into the pressure plugs 47 incorporated with the housing 21 of the cassette according to the invention when the moveable carriage 63 has displaced into the pumping position. A seal 46 is mounted around the pressure plugs 47 incorporated with the housing so as to ensure airtight contact with the teats in the pumping position of the moveable carriage 63.

At the conclusion of use, the linear actuator 85 controlling the displacement of the moveable carriage 63 displaces the latter in the direction of translation T from the pumping position to the rest position so as to unclamp the irrigation 1$i$ and aspiration 1$a$ pumping segments between the shoes and the rollers respectively of the irrigation pump and of the aspiration pump. The position sensors 90 fixed to the chassis 61 monitor the displacement of the carriage 63 in the direction of translation T. An abutment is fixed to the chassis 61 to stop the displacement of the carriage in the rest position.

The linear actuator controlling the displacement of the cassette holder 65 thereafter displaces the latter into the cassette ejection position so as to move the irrigation 11$i$ and aspiration 11$a$ pumping segments away from the shoes 53$i$, 53$a$ and the wheels 54$i$, 54$a$ with rollers respectively of the irrigation pump and of the aspiration pump. The position sensors 88 fixed to the chassis 61 monitor the displacement of the cassette holder 65 in the plane P perpendicular to the direction of translation T. An abutment 64 is fixed to the chassis to stop the displacement of the cassette holder in the cassette ejection position.

To remove the cassette from the irrigation and aspiration machine by hand, the locking means 73 mounted pivotably with respect to the cassette holder 65 is actuated by an abutment 75 fixed to the chassis 63 so as to pivot with respect to the cassette holder 65 when the latter displaces parallel to the plane P perpendicular to the direction of translation T, from the cassette insertion position to the cassette ejection position. The compression springs 62 carried by the cassette holder then eject the cassette from the cassette holder. The irrigation and aspiration machine is ready to be used with a fresh cassette.

The invention claimed is:

1. An irrigation and aspiration machine used in endoscopy, comprising a cassette intended to be inserted into an irrigation or aspiration machine used in endoscopy, said cassette comprising:

at least one of an irrigation tube and an aspiration tube, each tube having an elbow, a support furnished with one or with two inlet plugs, and with one or with two outlet plugs, the tube or each of the two tubes forming an elbow for engaging with the inlet and outlet plug or the two inlet and outlet plugs in a respectively incoming and outgoing direction of flow and forming a segment of irrigation or of aspiration pumping in the incoming direction of flow, wherein the support comprises a base and a T-shaped guide protruding from an end of the base, wherein a head of the T is shaped so as to protect the elbow of each tube and a body of the T being shaped as a slot guiding the tube or the two tubes in the outgoing direction of flow, wherein the T guide runs between the inlet plug or the two inlet plugs so as to form the segment of at least one of irrigation and aspiration pumping on at least one side of the slot between each inlet plug and the head of the T, said machine comprising a peristaltic irrigation pump with a first shoe mounted in correspondence with a first wheel with rollers, a chassis, the first shoe being mounted on the chassis, and a carriage, the first wheel with rollers being mounted on the carriage, wherein the carriage is moveable with respect to the chassis in a direction of translation between a rest position in which the first shoe is unclamped with respect to the rollers of the first wheel and a pumping position in which the first shoe is reclamped with respect to the rollers of the first wheel, a cassette holder mounted on the chassis, wherein the cassette holder extends in a plane perpendicular to the direction of translation and passing between the first shoe and the first wheel with rollers of the irrigation pump, and a peristaltic aspiration pump with a second shoe mounted in correspondence with a second wheel with rollers, the second shoe being mounted on the chassis and the second wheel with rollers being mounted on the carriage so as to unclamp or reclamp said second shoe with respect to said rollers of the second wheel in the direction of translation upon the unclamping or reclamping of the second shoe, with respect to the rollers of the first wheel of the peristaltic irrigation pump in the rest position or the pumping position, the plane in which the cassette holder extends passing likewise between the second shoe and the second wheel with rollers of the peristaltic aspiration pump, wherein the cassette holder is mounted moveably with respect to the chassis in the direction of translation, so as to be driven in translation by the carriage when the latter is displaced from the rest position to the pumping position, and so as to be displaced parallel to a plane perpendicular to the direction of translation, between a cassette insertion position where the cassette holder is close to the shoes and wheels with rollers of the peristaltic irrigation and aspiration pumps and a cassette ejection position where the cassette holder is away from said shoes and said wheels with rollers, wherein said insertion and ejection positions are defined respectively by a first and a second abutment with respect to the chassis.

2. The irrigation and aspiration machine with cassette as claimed in claim 1, wherein the cassette holder is provided with a means of locking mounted pivotably with respect to the cassette holder so as to be actuated by an abutment fixed to the chassis and pivot with respect to the cassette holder when the latter displaces parallel to the plane perpendicular to the direction of translation, from the cassette insertion position to the cassette ejection position.

3. The irrigation and aspiration machine with cassette as claimed in claim 1, wherein the shoes of the peristaltic irrigation and aspiration pumps are mounted moveably with respect to the chassis in the direction of translation.

4. The irrigation and aspiration machine with cassette as claimed in claim 1, wherein it comprises air pressure sensors communicating with air pressure plugs carried by the moveable carriage.

5. The irrigation and aspiration machine with cassette as claimed in claim 1, wherein the carriage carries two or three shutters moveable with respect to the carriage in the direction of translation.

6. The irrigation and aspiration machine with cassette as claimed in claim 1, wherein the carriage carries cassette recognition fingers moveable with respect to the carriage in the direction of translation.

7. The irrigation and aspiration machine with cassette as claimed in claim 1, wherein it comprises a means of centering mounted on the carriage so as to be displaced with the carriage in the direction of translation from the rest position to the pumping position and after the cassette holder has come near to the shoes of the irrigation and aspiration pumps in the cassette insertion position.

* * * * *